United States Patent [19]

Hargis

[11] Patent Number: 4,721,810
[45] Date of Patent: Jan. 26, 1988

[54] CATALYTIC ALKYLATION OF AROMATIC AMINES WITH ETHERS

[75] Inventor: Duane C. Hargis, Baton Rouge, La.

[73] Assignee: Ethyl Corporation, Richmond, Va.

[21] Appl. No.: 618,005

[22] Filed: Jun. 6, 1984

[51] Int. Cl.$^4$ .................. C07C 89/02; C07C 85/24
[52] U.S. Cl. ..................................... 564/399; 564/409
[58] Field of Search ............... 564/402, 401, 409, 399, 564/474, 479, 480; 548/577, 543, 570, 532, 563, 565

[56] References Cited

U.S. PATENT DOCUMENTS

| 2,012,801 | 8/1935 | Andrussow et al. | 260/128 |
| 2,389,500 | 11/1945 | Goshorn | 564/479 |
| 3,086,017 | 4/1963 | Denton | 260/247 |
| 3,853,887 | 12/1974 | Pike et al. | 548/532 |
| 3,868,420 | 2/1975 | Evans et al. | 260/578 |
| 4,418,005 | 11/1983 | Dodd et al. | 502/217 |
| 4,605,766 | 8/1986 | Hargis | 564/409 |

FOREIGN PATENT DOCUMENTS

| 0148009 | 7/1985 | European Pat. Off. . |
| 0768142 | 7/1934 | France . |
| 0851178 | 1/1940 | France . |
| 53-90227 | 8/1978 | Japan . |
| 0809752 | 3/1959 | United Kingdom . |

OTHER PUBLICATIONS

*Chemical Abstracts*, vol. 36, No. 1957(2), (1942).

Primary Examiner—Charles F. Warren
Assistant Examiner—Elizabeth A. Hanley
Attorney, Agent, or Firm—Donald L. Johnson; John F. Sieberth

[57] ABSTRACT

Aromatic amines are alkylated by reaction with an acyclic ether or an unstrained cyclic ether in the presence of a B-subgroup metal oxide alkylation catalyst, preferably a Group IV-B metal oxide with or without a minor proportion of a Group VI-B or Group VIII metal oxide, so that alkylation of the aromatic amine occurs. Under most reaction conditions ether alkylating agents such as diethyl ether not consumed in the alkylation reaction pass through the reaction zone undecomposed and thus can be readily recovered for recycle or other use.

13 Claims, No Drawings

CATALYTIC ALKYLATION OF AROMATIC AMINES WITH ETHERS

FIELD

This invention relates to an improved catalytic process for the alkylation of aromatic amines.

BACKGROUND

Numerous methods, processes, and catalysts have been described for alkylating aromatic amines to provide valuable and useful chemical products. However, the previous suggestions have various defects including lack of selectivity of the desired product, poor conversion of the aromatic amine, and excessive deterioration of the alkylating agent which then cannot be recovered for recycle or other use.

THE INVENTION

In accordance with this invention an efficacious process for alkylating alkylatable aromatic amines is provided. In general, the process comprises the step of reacting (a) an aromatic amine having at least one replaceable hydrogen atom on an amine group or on an aromatic ring carrying an amino group or both, with (b) an ether in the presence of a B-subgroup metal oxide alkylation catalyst so that alkylation of the aromatic amine occurs. When effecting nuclear alkylation (i.e., alkylation on the ring), best results are achieved when the aromatic amine has at least one primary amino group on an aromatic ring and has a replaceable hydrogen on the ring in at least an ortho or para position relative to such amino group.

A preferred embodiment of this invention involves using as the catalyst a metal oxide alkylation catalyst consisting essentially of at least about 70 mole % (i.e., about 70 to 100%) of a Group IV-B metal oxide, most preferably a titanium oxide (especially $TiO_2$) and up to about 30 mole % (i.e., 0 to about 30%) of (i) a Group VI-B metal oxide, most preferably a molybdenum oxide (especially $MoO_3$) or (ii) a Group VIII metal oxide, most preferably an iron oxide (especially $Fe_2O_3$), or (iii) a mixture of (i) and (ii). These and still other preferred embodiments of this invention will be still further apparent from the ensuing description and appended claims.

A particular advantage of my process is that under most reaction conditions ether alkylating agents such as diethyl ether not consumed in the alkylation reaction pass through the reaction zone undecomposed and thus can be readily recovered for recycle or other use. In addition, my process involves use of catalysts which are easily prepared, and which in many cases have superior catalytic activity and long useful lives.

Another feature of this invention is that the nature of the alkylation product can be varied considerably depending upon the nature of the B-subgroup metal oxide alkylation catalyst used. For example, to achieve substantial alkylation on the primary amino group ($-NH_2$) on an aromatic ring which itself contains one or more replaceable hydrogen atoms, it is desirable to employ a Group IV-B metal oxide alkylation catalyst such as $TiO_2$, $ZrO_2$, or the like. In fact, with a zirconia catalyst, reaction between aniline and diethylether at 325° C. resulted in 95% conversion and 94.5% yield of N-ethylated products. To increase the proportion of ring alkylation relative to nitrogen alkylation, use may be made as the alkylation catalyst of a Group IV-B metal oxide combined with a minor proportion (usually 20% by weight or less) of a Group VI-B metal oxide such as $MoO_3$, $WO_3$ or the like. Use of a minor proportion of a Group VIII metal oxide such as $Fe_2O_3$ in combination with a Group IV-B metal oxide alkylation catalyst also tends to increase the ratio of ring alkylation to nitrogen alkylation. When a Group II-B metal oxide alkylation catalyst such as ZnO is employed by itself as the catalyst, alkylation tends to be focused on the nitrogen atom.

The reaction conditions used also tend to affect the course of the reaction. In general, when an opportunity exists for both ortho and para alkylation to occur, the use of higher reaction temperatures tends to promote an increase in orthoalkylation especially when using $TiO_2$-based alkylation catalysts. For example, reaction between aniline and diethylether using a 90% $TiO_2$-10% $Fe_2O_3$ catalyst gave an o-ethylaniline/p-ethylaniline ratio of 4.3 at 350° C., whereas at 375° C. the ratio was 5.7. Likewise, the addition of water to the feed stream tends to increase the ortho/para ratio of the ring alkylated products.

According to the present invention, ethers have been found to be very effective for alkylating various alkylatable aromatic amines in the presence of a B-subgroup metal oxide alkylation catalyst. While product selectivity is usually at least as good as the processes known to the prior art, this invention also offers the additional advantage of making possible conversion rates somewhat higher than with processes disclosed in the prior art. Furthermore, in the process of this invention it is possible to achieve almost complete recovery of the ether which passes through the reaction zone without participating in the alkylation reaction. This of course, enables the ether to be reused in the present process or to be used for other purposes.

The present invention is carried out at an elevated temperature conventional for catalytic alkylation processes. The temperature of reaction for the present process is usually about 200° C. or higher, preferably 300° C. or higher. More preferably, the process of the present invention is carried out at an elevated temperature in the range of about 350°–450° C. While higher temperatures may be used, the temperature used should take into consideration the thermal decomposition temperatures of the reactants and products as well as the effect of temperature on the activity of the particular heterogeneous catalyst system being employed. In general, the most preferred temperatures for the process fall in the range of from about 350° to about 425° C.

When the process of the present invention is carried out as further described below, the conversion of aromatic amines such as aniline, toluidine, xylidine, and more complex aromatic amines is usually in the range of from less than 5 to as much as 30% or more. The 30% or more figure is considered very satisfactory for most catalytic alkylation processes. In view of the recoverability of the alkylating agent of the present invention, conversions in this range are especially advantageous since the process can be made much more economical with recovery of such a reactant. The process of the present invention is suitably carried out at atmospheric pressure but may be carried out at superatmospheric or subatmospheric pressures.

Numerous aromatic amines are usable according to the process of this invention. Typical aromatic amines usable as starting materials in my process include the single ring compounds such as aniline, o-toluidine, m-toluidine, p-toluidine, o-ethylaniline, m-ethylaniline, p-ethylaniline, o-isopropylaniline, m-isopropylaniline, p-isopropylaniline, 2,3-xylidine, 2,4-xylidine, 2,5-xylidine, 2,6-xylidine, 3,4-xylidine, 3,5-xylidine, 2,3-diethylaniline, 2,4-diethylaniline, 2,5-diethylaniline, 2,6-diethylaniline, 3,4-diethylaniline, 3,5-diethylaniline, 2,3-diisopropylaniline, 2,4-diisopropylaniline, 3,5-diisopropylaniline, and the like. Also usable according to the process of the present invention are the N-alkylated aromatic amines such as N-methylaniline, N-ethylaniline, N-isopropylaniline, N,N-dimethylaniline, N,N-diethylaniline, N,N-diisopropylaniline, N-methyl-o-toluidine, N-methyl-2,3-xylidine, N-methyl-2,4-xylidine, N-methyl-2,5-xylidine, N-methyl-3,5-xylidine, N,N-dimethyl-o-toluidine, N,N-dimethyl-m-toluidine, N,N-dimethyl-p-toluidine, N,N-dimethyl-2,3-xylidine, N,N-dimethyl-2,4-xylidine, N,N-dimethyl-2,5-xylidine, N,N-dimethyl-3,5-xylidine, N-ethyl-o-toluidine, N-ethyl-m-ethylaniline, N-ethyl-p-ethylaniline, N-ethyl-2,3-diethylaniline, N-ethyl-2,4-diethylaniline, N-ethyl-2,5-diethylaniline, N-ethyl-3,5-diethylaniline, N,N-diethyl-o-ethylaniline, N-ethyl-3,5-diethylaniline, N,N-diethyl-o-ethylaniline, N,N-diethyl-m-ethylaniline, N,N-diethyl-p-ethylaniline, and the like. Also usable in the process of this invention are multiple ring compounds such as diphenylamine, 4-aminobiphenyl, 1-naphthylamine, 2-naphthylamine, 1-anthrylamine, 1-phenanthrylamine, 1,4-diaminonaphthalene, 1,5-diaminonaphthalene, and the like. Similarly the aromatic diamines, triamines, and other polyamines are usable. Examples of such compounds include 2,4-toluenediamine, 2,5-toluenediamine, 1,3-diaminobenzene, 4,4'-methylenebisaniline, 1,3,5-triaminobenzene, and the like.

Of the above described aromatic amines, the single ring aromatic amines are preferred. Aniline and ring alkylated anilines are the more preferred of the single ring aromatic amines. Most preferred are aniline, one or a mixture of two or more toluidine isomers or one or a mixture of two or more xylidine isomers.

Various ethers are usable in the present process. These include acyclic ethers, i.e., ethers in which the ether oxygen is not in a ring system, and unstrained cyclic ethers. Useful acyclic ethers include alkyl ethers, (either straight or branched chain), cycloalkyl ethers, aromatic ethers, and ethers which are mixtures of these types. A preferred class of ethers are the dialkyl ethers where the alkyl groups are either the same or different and at least one of them is a primary alkyl group. These include dimethyl ether, dibutyl ether, ethyl propyl ether, ethyl octyl ether, diisobutyl ether, ethyl methyl ether, diisopropyl ether, heptyl methyl ether, methyl tert-butyl ether, and the like. More preferred from the standpoint of reaction selectivity are the dialkyl ethers where the alkyl groups are the same such as dimethyl ether, diethyl ether, di-n-propyl ether, di-n-butyl ether, diisobutyl ether, di-n-pentyl ether, and the like. Especially preferred are the di-lower alkyl ethers (i.e., each alkyl group has up to about six carbon atoms), especially those in which the alkyl groups are identical and are primary alkyl groups.

Various unsaturated acyclic ethers are also usable according to the present invention. These include divinyl ether, diallyl ether, dicrotyl ether, and the like.

Various acyclic aromatic ethers (e.g., aryl and aralkyl ethers) are also usable with the present invention. These include dibenzyl ether, diphenyl ether, benzyl phenyl ether, and other such ethers. Also usable according to the present invention are the mixed alkyl and aromatic ethers such as anisole, ethyl phenyl ether, ethyl p-tolyl ether, hexyl phenyl ether, methyl benzyl ether, 2,6-dimethoxypyridine, 2,4-dimethoxypyrimidine, and the like.

Also usable according to the present invention are the acyclic cycloalkyl ethers such as dicyclopentyl ether, dicyclohexyl ether, and the like. Also mixed cycloalkyl ethers are usable, such as cyclopentyl cyclohexyl ether. Furthermore, mixed ethers having a cycloalkyl substituent and another substituent are also usable according to the present invention. These include, for example, methyl cyclopentyl ether, benzyl cyclohexyl ether, ethyl cyclopropylcarbinyl ether, and the like.

Also usable according to the present invention are the glycol ethers such as the ethylene glycol ethers and propylene glycol ethers including 1,2-dimethoxyethane, 1,2-diethoxyethane, 1,2-dimethoxypropane, 1,3-diethoxypropane, and the like.

Cyclic ethers, namely ethers in which an oxygen atom is in a ring system, are also suitable for the practice of this invention provided the ring system of the cyclic ether contains only carbon and from 1 to 3 oxygen atoms in an unstrained ring (i.e., the ring contains at least four carbon atoms and at least one oxygen atom bonded to two separate carbon atoms of the ring). Examples of such cyclic ethers include tetrahydrofuran, 2-methyltetrahydrofuran, 3-methyltetrahydrofuran, tetrahydro-2-furancarbinol, 2-ethoxymethyl tetrahydrofuran, 2-butoxymethyl tetrahydrofuran, tetrahydrofuroic acid, methyl tetrahydrofuroate, tetrahydropyran, 2-methyltetrahydropyran, furan, dihydrofuran, pyran, dihydropyran, and the like. In the case of such cyclic ethers as tetrahydrofuran, tetrahydropyran and their suitably substituted congeners, reaction with primary aromatic amines such as aniline and nuclear alkylanilines (e.g., toluidines, xylidines, o-, m-, p-ethylaniline, 2,3-, 2,4-, 2,5-, 2,6-, 3,4- and 3,5-diethylanilines, etc.) results in gem-dialkylation of the nitrogen atom whereby N-arylated cyclic amines are formed. In some instances, this reaction proceeds with high conversions of the aromatic amine and produces the product in very high yield. For example, reaction between tetrahydrofuran and aniline at 250° C. using a $TiO_2$ catalyst (LHSV of 0.2 per hour) gave a 98% conversion of aniline with a 97% yield of 1-phenyl-pyrrolidine. Similarly, tetrahydropyran and aniline when reacted at 300° C. over a $TiO_2$ catalyst (LHSV of 0.2 per hour) resulted in a 74% aniline conversion with a 98% yield of 1-phenylpiperidine.

Generally speaking, most ethers having the linkage C-O-C are usable according to the present invention although in some cases unreactive types of ethers may be encountered. Thus, I utilize in the present process only ethers that are coreactive with the alkylatable aromatic alkaline so that alkylation occurs. In this connection, the term "alkylation" is used herein in a generic sense to indicate that an organic group of the ether reactant, whether alkyl, aryl or etc., is introduced into the molecule of the aromatic amine reactant.

The present invention is capable of being carried out in either a batch or continuous operation mode according to the available equipment and intentions of the operator.

According to the invention, various catalysts may be used so long as the catalyst consists essentially of a B-subgroup metal oxide of suitable activity in the alkylation reaction under consideration. As is well known, Group I-B is composed of copper, silver and gold whereas Group II-B is composed of zinc, cadmium and mercury. Scandium, yttrium and the lathanide and actinide series make up Group III-B. Group IV-B consists of titanium, zirconium and hafnium, Group V-B consists of vanadium, niobium and tantalum, Group VI-B consists of chromium, molybdenum and tungsten, and Group VII-B consists of manganese, technetium and rhenium. Various oxides of such metals that are viable catalysts for the alkylation are within the ambit of this invention. Aromatic amine alkylation catalysts composed of mixtures of two or more different oxides of the same B-subgroup metal (e.g., $TiO_2$ and $Ti_2O_3$, etc.), composed of oxides of two or more different metals of the same B-subgroup (e.g., $TiO_2$ and $ZrO_2$; $TiO_2$, $ZrO_2$ and $HfO_2$, etc.), and composed of oxides of two or more metals of different B-subgroups (e.g., $TiO_2$ and $MoO_3$, $TiO_2$ and $WO_3$, $TiO_2$ and $ZnO$, etc.) may also be used. Various other oxides usable as additional components of the catalysts of the present invention such as one or more oxides of aluminum, antimony, barium, beryllium, bismuth, calcium, cobalt, gallium, germanium, iron, lead, magnesium, nickel, osmium, potassium, silicon, sodium, tin, and the like may be prepared by any of the known means and combined with the B-subgroup metal oxide catalysts according to the invention. Catalysts composed of one or more B-subgroup metal oxides in combination with one or more non-B-subgroup metal oxides should predominate (on a molar basis) in the B-subgroup metal oxide(s). In fact, such mixed oxide catalysts preferably contain at least 70 mole % of one or more B-subgroup metal oxides and no more than about 30 mole % of one or more non-B-subgroup metal oxides.

As noted above, it is important when practicing this invention to use an active alkylation catalyst for the process. In this connection, the thermal history of the catalyst appears to be of importance to its activity. For example, a highly active titania catalyst for the process of this invention after having been heated to 450° C. was found to have lost a substantial amount of its catalytic activity for the process. And after heating the catalyst to 650° C., this catalyst was found to be totally ineffective for use in my process. Thus any given commercially available B-subgroup metal oxide catalyst may or may not be active in the process of this invention depending upon whether or not it was calcined and if so, whether the calcining temperature was high enough to destroy its catalytic activity for use in the process of this invention. Thus in selecting commercially available B-subgroup metal oxides for use in my process, one should attempt to secure materials that have not been calcined at excessively high temperatures that render them unsuitable in the present process. In cases where the manufacturers decline to supply such thermal history information, one should secure and test in the present process a variety of samples of candidate B-subgroup metal oxide catalysts and select one or more having the best or optimum activity for the particular aromatic amine alkylation under consideration. As an example, samples of two different $TiO_2$ catalysts were obtained from the same commercial manufacturer. X-ray diffraction analysis showed that both were in the anatase phase and indicated that they were identical materials. One of these was found to be a highly active catalyst for use in my process. The other was totally inactive.

Methods for the manufacture of oxides of B-subgroup metals are known and reported in the literature. When utilizing such procedures care should be taken to avoid heating the oxide catalyst to a temperature which destroys or substantially diminishes its catalytic activity in my alkylation process. The catalyst may be supported on or impregnated onto a suitable inert carrier although this is ordinarily unnecessary.

Although the process can be carried out in the liquid phase, it is preferable to conduct the process in the vapor phase using a fixed-bed or a moving or fluidized bed of the catalyst.

The present invention will be still further understood by a review of the following illustrative examples of the best mode of the invention of which I am now aware, in which all of the percentages are expressed on a weight basis unless otherwise specified.

In the ensuing examples use was made of a tubular reactor positioned within an Ohio Thermal wire wound tubular furnace, model T11C-0432. The muffle tube of the furnace was 1½ inches inside diameter and 12 inches long, constructed of fused alumina. A ¼ inch inside diameter thermocouple well was provided adjacent to the heating element. The thermocouple was used to control the series 4DA controller which has a range of 200°–1100° C. The reactor itself was a 19 inch long, 1 inch inside diameter stainless steel tube fitted with an internal thermocouple well. The reactor tube was fitted for supply of helium gas from one line and a second line connected to a Milton Roy pump. The second line fed reactants from a reservoir attached thereto. A water condenser below the reactor tube and an ice bath were used to collect liquid in glassware in the ice bath. The vapors transmitted from the glassware in the ice bath were directed to a dry ice bath and the outlet thereof was connected directly to a gas chromatography unit and then to a wet test meter.

The following procedure was used for all of the runs given in the tables below. The reactor tube was filled with 5 millimeter glass beads to define the catalyst bed location. A weighed amount of catalyst was then supplied to the catalyst bed area and additional 5 millimeter beads were used to fill the tube to the top of the furnace. All equipment was properly purged and flushed according to good standard laboratory practice. The desired feed for the run was added to the reservoir and the pump and inlet tube as necessary. The ice water bath and dry ice bath were attached, and the helium flush was started at the rate of 20–30 cc per minute during furnace warmup and stabilization. To start a run, the helium was turned off, and the feed pump was turned on at the desired feed rate. The thermocouple temperatures were recorded along with the feed level and the wet test meter readings. The sampling times were also noted. The product gases were directed to the sample loop of the GC sampling valve and injected onto a 10'×⅛" Poropak TM R column. The traps were removed and immediately replaced with a second set. The liquid samples were combined and weighed. To terminate the run, the feed pumps were turned off and drained for about five minutes before removing the residue therein. Thereafter, the helium flush was again turned on at about 20–30 cc per minute and the furnace was turned off. After cooling to room temperature, the reactor tube was removed for catalyst inspection, analysis, and/or replacement. The catalysts were unsupported—i.e., an inert support or carrier for the catalyst was not used in any of the runs. Except where otherwise noted, the operations were conducted using a liquid hourly space velocity (LHSV) of 0.2 hr$^{-1}$.

Table I summarizes the results of a number of runs at various temperatures using a variety of individual B-subgroup metal oxide catalysts in the vapor phase alkylation of aniline with diethyl ether. The reactants were employed in a ratio of 2.5 moles of diethyl ether per mole of aniline. The gaseous products referred to in the tables are uncondensables and the magnitude of this figure serves as an indication of the extent of decomposition, if any, that occurred during the run. All but one of the catalysts used in these runs were obtained from commercial sources, and are identified as follows:

Catalyst No. 21- $TiO_2$; Harshaw Ti-X-L2873-23-10. It was of the anatase crystallographic form and had a surface area of 143 m$^2$/g.

Catalyst No. 22- $TiO_2$; Harshaw Ti-0720. It was of the anatase crystallographic form and had a surface area of 112 m$^2$/g.

Catalyst No. 36- $TiO_2$; Harshaw Ti-X-L2873-23-10. It was of the anatase crystallographic form and had a surface area of 153 m$^2$/g.

Catalyst No. 40- $ZrO_2$; Harshaw Zr-0304. It had a surface area of 46.1 m$^2$/g.

Catalyst No. 44- ZnO; Harshaw Zn 0701.

Catalyst No. 45- $Ti_2O_3$; Cerac, Inc. T-1157. It had a surface area of 0.2 m$^2$/g.

Catalyst No. 56- TiO; Cerac, Inc. T-1154. It had a surface area of less than 0.1 m$^2$/g.

The other catalyst referred to in Table I was synthesized as reported in Example 1.

EXAMPLE 1

Preparation of Catalyst No. 24—$TiO_2$

Titanium isopropoxide (155.15 g) was dissolved in 200 mL of isopropanol and heated to 60° C. with stirring. Distilled water (42.5 mL) was added dropwise maintaining the temperature below 70° C. to precipitate titania. Excess isopropanol was evaporated off under a dry nitrogen stream at 50°–60° C. to give a thick paste. The paste was extruded through a 50 cc plastic syringe and air-dried overnight. The extrusions were oven-dried at 110° C. for 2 hours and then calcined at 450° C. overnight to give 41.7g of finished catalyst.

TABLE I

| Alkylations Using Individual B-Subgroup Metal Oxide Catalysts | | | | | | | | | | | | | | | | |
|---|---|---|---|---|---|---|---|---|---|---|---|---|---|---|---|---|
| Run Number | 1 | 2 | 3 | 4 | 5 | 6 | 7 | 8 | 9 | 10 | 11 | 12 | 13 | 14 | 15 | 16 |
| Catalyst | $TiO_2$ | $TiO_2$ | $TiO_2$ | $TiO_2$ | $TiO_2$ | $TiO_2$ | $TiO_2$ | $TiO_2$ | $TiO_2$ | $TiO_2$ | $TiO_2$ | $ZrO_2$ | $ZrO_2$ | $ZrO_2$ | $ZrO_2$ | ZnO |
| Catalyst Number | 21 | 21 | 22 | 22 | 36 | 36 | 36 | 36 | 24 | 24 | 24 | 40 | 40 | 40 | 40 | 44 |
| Temperature, °C. | 250 | 300 | 250 | 300 | 300 | 325 | 350 | 375 | 300 | 350 | 400 | 300 | 325 | 350 | 375 | 325 |
| Aniline Conversion, % | 54 | 87 | 69 | 95 | 59 | 70 | 71 | 64 | 38 | 88 | 68 | 94 | 94 | 77 | 44 | 37 |
| Ether Conversion, % | 18 | 45 | 19 | 61 | 22 | 35 | 54 | 72 | 9 | 60 | 99 | 58 | 89 | 99.5 | 99.9 | 17 |
| Product Distribution, wt. percent | | | | | | | | | | | | | | | | |
| N—et aniline | 64.4 | 38.2 | 51.9 | 16.7 | 63.7 | 52.8 | 51.5 | 51.5 | 82.7 | 50.0 | 22.0 | 69.1 | 63.4 | 79.5 | 90.5 | 86.4 |
| o-et aniline | 2.6 | 2.0 | 0.9 | 1.4 | 0.7 | 2.3 | 4.9 | 9.8 | 4.1 | 3.5 | 21.1 | — | 0.2 | 0.7 | 1.8 | — |
| p-et aniline | 4.5 | 1.9 | 3.5 | 3.4 | 0.9 | 1.3 | 1.6 | 2.3 | 4.5 | 1.3 | 9.2 | — | 0.2 | 0.4 | 0.7 | — |
| N,N—di-et aniline | 11.8 | 18.7 | 12.9 | 6.9 | 17.8 | 17.9 | 13.1 | 7.8 | 5.2 | 20.3 | 1.8 | 30.4 | 31.1 | 15.3 | 5.7 | 2.1 |
| 2,6-di-et aniline | 2.9 | 2.2 | 3.2 | 6.1 | 2.4 | 2.8 | 3.9 | 7.4 | — | 2.6 | 13.8 | — | — | — | — | — |
| Other ring di-et anilines | 7.1 | 17.1 | 12.9 | 22.8 | 8.8 | 13.5 | 15.3 | 11.9 | — | 14.2 | 11.8 | — | — | — | — | — |
| Ring tri-et anilines | 3.3 | 12.4 | 12.2 | 30.4 | 4.0 | 6.1 | 5.1 | 3.4 | — | 4.9 | 5.3 | — | — | — | — | — |
| Others | 3.3 | 7.6 | 2.5 | 12.3 | 1.6 | 3.2 | 4.5 | 5.9 | 3.5 | 3.2 | 15.0 | 0.5 | 5.2 | 4.1 | 1.4 | 11.5 |
| N—alkylation, % | 76.2 | 56.9 | 64.8 | 23.6 | 81.5 | 70.7 | 64.6 | 59.3 | 87.9 | 70.3 | 23.8 | 99.5 | 94.5 | 94.8 | 96.2 | 88.5 |
| Ring alkylation, % | 10.0 | 6.1 | 7.6 | 10.9 | 4.0 | 6.4 | 10.5 | 19.5 | 8.6 | 7.4 | 44.1 | — | 0.4 | 1.2 | 2.5 | — |
| Di-, tri-, & others, % | 13.7 | 37.1 | 27.6 | 65.5 | 14.4 | 22.8 | 24.8 | 21.2 | 3.5 | 22.3 | 32.1 | 0.5 | 5.2 | 4.1 | 1.4 | 11.5 |
| Ratio of o-et to p-et | 0.6 | 1.1 | 0.3 | 0.4 | 0.8 | 1.8 | 3.1 | 4.3 | 0.9 | 2.7 | 2.3 | — | 1.0 | 1.8 | 2.6 | — |
| Gaseous products, mL/hr | 5 | 55 | 0 | 75 | 20 | 70 | 200 | 400 | 25 | 205 | 600 | 320 | 800 | 1370 | 1570 | 160 |
| Run Number | 17 | 18 | 19 | 20 | 21 | 22 | 23 | 24 | 25 | 26 | 27 | 28 | 29 | 30 | 31* | 32 |
| Catalyst | ZnO | ZnO | ZnO | $Ti_2O_3$ | $Ti_2O_3$ | $Ti_2O_3$ | $Ti_2O_3$ | TiO | TiO | TiO | TiO | $TiO_2$ | $TiO_2$ | $TiO_2$ | $TiO_2$ | $TiO_2$ |
| Catalyst Number | 44 | 44 | 44 | 45 | 45 | 45 | 45 | 56 | 56 | 56 | 56 | 22 | 22 | 22 | 22 | 22 |
| Temperature, °C. | 350 | 375 | 400 | 300 | 325 | 350 | 375 | 300 | 350 | 375 | 400 | 325 | 350 | 375 | 375 | 400 |
| Aniline Conversion, % | 35 | 40 | 30 | 10 | 15 | 23 | 30 | 7 | 20 | 29 | 30 | 95 | 91 | 86 | 71 | 65 |
| Ether Conversion, % | 38 | 67 | 94 | — | 1 | 1.4 | 9 | 1 | 5 | 10 | 18 | 77 | 93 | 98 | 76 | 96 |
| Product Distribution, wt. percent | | | | | | | | | | | | | | | | |
| N—et aniline | 79.8 | 68.5 | 52.7 | 97.9 | 96.3 | 92.5 | 87.0 | 98.8 | 96.8 | 95.3 | 87.8 | 11.5 | 5.1 | 3.3 | 26.5 | 12.0 |
| o-et aniline | — | 3.9 | 1.1 | — | — | — | 0.6 | — | — | — | 1.1 | 2.4 | 6.1 | 12.0 | 12.2 | 22.9 |
| p-et aniline | 0.4 | 0.4 | 0.1 | — | — | — | — | — | — | — | — | 4.1 | 6.2 | 8.8 | 7.8 | 10.6 |
| N,N—di-et aniline | 2.2 | 2.5 | 2.1 | 2.1 | 3.1 | 6.0 | 6.3 | 1.2 | 3.2 | 3.6 | 3.1 | 3.1 | 0.6 | 0.3 | 2.5 | 0.6 |
| 2,6-di-et aniline | 4.0 | 4.0 | 5.5 | — | — | — | — | — | — | — | — | 3.4 | 11.7 | 20.4 | 25.7 | 12.1 | 21.5 |
| Other ring di-et anilines | 2.0 | 2.7 | 8.2 | — | — | — | — | — | — | — | — | 3.6 | 17.1 | 7.9 | 4.4 | 13.8 | 5.6 |
| Ring tri-et anilines | — | 1.2 | 6.8 | — | — | — | — | — | — | — | — | 32.4 | 30.3 | 17.8 | 9.3 | 7.7 |
| Others | 11.6 | 16.6 | 23.5 | — | 0.6 | 1.6 | 6.1 | — | — | — | 1.1 | 0.8 | 17.7 | 23.6 | 27.8 | 15.8 | 19.0 |
| N—alkylation, % | 82.0 | 71.0 | 54.8 | 100.0 | 99.4 | 98.5 | 93.3 | 100 | 100 | 98.9 | 90.9 | 14.6 | 5.7 | 3.6 | 29.0 | 12.6 |
| Ring alkylation, % | 4.4 | 8.3 | 6.7 | — | — | — | 0.6 | — | — | — | 1.1 | 18.2 | 32.7 | 46.5 | 32.1 | 55.0 |
| Di-, tri-, & others, % | 13.6 | 20.5 | 38.5 | — | 0.6 | 1.6 | 6.1 | — | — | 1.1 | 7.8 | 67.2 | 61.8 | 50.0 | 38.9 | 32.3 |
| Ratio of o-et to p-et | — | 9.8 | 11.0 | — | — | — | — | — | — | — | — | 0.6 | 1.0 | 1.4 | 1.6 | 2.2 |
| Gaseous products, mL/hr | 340 | 820 | 1560 | 10 | 20 | 50 | 50 | 0 | 15 | 30 | 70 | 225 | 315 | 410 | 670 | 730 |

*The LHSV was 0.4 per hour.

In another group of runs the vapor phase alkylation of aniline with diethyl ether was performed in the same manner using various catalysts composed of two different metal oxides, one or both of which was a B-subgroup metal oxide. One of these mixed metal oxide catalysts was obtained from a commercial source. The others were prepared by me.

The commercial catalyst, Catalyst No. 50, was a mixed $ZrO_2$-$TiO_2$ catalyst from Cerac, Inc., Z-1079. It had a surface area of less than 0.1 m²/g.

Examples 2 through 8 describe the procedures used by me in synthesizing the mixed metal oxide catalysts.

EXAMPLE 2

Preparation of Catalyst No. 19—$TiO_2$—5% $MoO_3$ 155.25 Grams of titanium isopropoxide was dissolved in 200 mL of isopropanol and the solution was heated to 60° C. with stirring. Distilled water (42.5 mL) was added dropwise while maintaining the temperature below 70° C. to precipitate titania. Then 6.15 mL of a 10% aqueous solution of $(NH_4)_2MoO_4$ was added and excess solvent evaporated off under a dry nitrogen stream at 60° C. The damp precipitate was moistened with distilled water to give a thick paste. This was extruded through a 50 cc plastic syringe. The extrusions were air-dried, then oven-dried for three hours at 110° C., and then calcined overnight at 450° C. to give 43.5 g of finished catalyst.

EXAMPLE 3

Preparation of Catalyst No. 25—$TiO_2$—10% $MoO_3$

A solution made from 155.25 g of titanium isopropoxide and 200 mL of isopropanol was heated to 60° C. with stirring. Distilled water (42.5 mL) was added dropwise while maintaining the temperature below 70° C. to precipitate titania. Then 12.3 mL of a 10% aqueous solution of $(NH_4)_2MoO_4$ was added with stirring and excess solvent evaporated off under a dry nitrogen stream at 50°-60° C. to give a thick paste. This was extruded through a 50 cc plastic syringe. The extrusions were air-dried for two hours, then oven-dried overnight at 100° C., and then calcined for eight hours at 450° C. to give 43.8 g of finished catalyst.

EXAMPLE 4

Preparation of Catalyst No. 26—$TiO_2$—5% $WO_3$

A solution of 77.63 g of titanium isopropoxide in 100 mL of isopropanol was heated to 60° C. with stirring. Distilled water (21.3 mL) was added dropwise while maintaining the temperature below 70° C. to precipitate titania. Then 12.35 g of a 10% aqueous solution of $(NH_4)_6H_2W_{12}O_{40}.xH_2O$ was added with stirring. Excess solvent was evaporated off under a dry nitrogen stream at 50°-60° C. to give a nearly dry powder. To this was added water to give a thick paste which was extruded through a 50 cc plastic syringe. The extrusions were air-dried for four hours, then oven-dried for three hours at 100° C., and then calcined at 450° C. overnight to give 22.7 g of finished catalyst.

EXAMPLE 5

Preparation of Catalyst No. 27—$TiO_2$—5% $Fe_2O_3$

A solution of 77.63 g of titanium isopropoxide in 100 mL of isopropanol was heated to 60° C. with stirring. Distilled water (21.3 mL) was added dropwise while maintaining the temperature below 70° C. to precipitate titania. To this slurry was added 53.16 g of a 10% aqueous solution of $Fe(NO_3)_3.9H_2O$ with stirring. Excess isopropanol and water were evaporated off by means of a dry nitrogen stream at 50°-60° C. to give a thick paste. Extrusions of the paste through a 50 cc plastic syringe were air-dried overnight, oven dried at 100° C. for four hours, and then calcined at 450° C. for four hours. This yielded 22.8 g of finished catalyst.

EXAMPLE 6

Preparation of Catalyst No. 32—$TiO_2$—10% $Fe_2O_3$

The procedure of Example 5 was repeated in the same fashion except that 106.32 g of the 10% aqueous solution of $Fe(NO_3)_3 9H_2O$ was added to the titania slurry. During the stripping at 50°-60° C., the solids began to granulate and turn dark brown before all of the isopropanol had been removed. This experiment yielded 22.3 g of a dense, black finished catalyst.

EXAMPLE 7

Preparation of Catalyst No. 35—$TiO_2$—20% $Fe_2O_3$

A solution of 77.63 g of titanium isopropoxide in 100 mL of isopropanol was heated to 60° C. with stirring. Distilled water (21.3 mL) was added dropwise while maintaining the temperature below 70° C. to precipitate titania. To this slurry was added 100 g of a 21.26 wt. % aqueous solution of $Fe(NO_3)_3.9H_2O$ with stirring. Excess isopropanol and water were evaporated off by means of a dry nitrogen stream at 40°-50° C. to give a thin paste. Further evaporation of water was conducted at low heat with a hot plate to give a thick paste. The paste was oven-dried at 100° C. overnight. The resulting large particles were crushed to less than 2 mm, then calcined at 450° C. for six hours to give 26.0 g of finished catalyst.

EXAMPLE 8

Preparation of Catalyst No. 38—$TiO_2$—10% $Fe_2O_3$

The procedure of Example 5 was repeated in the same manner except that 10.63 g of $Fe(NO_3)_3.9H_2O$ in 50 mL of water was used. After removing the excess solvent the thick paste of the catalyst was poured onto a flat surface and air-dried, then oven-dried at 100° C. overnight. Calcining at 450° C. for six hours gave 23.4 g of finished catalyst.

TABLE II

| | Alkylations Using Two Metal Oxides One or Both Being a B-Subgroup Metal Oxide Catalyst | | | | | | | |
|---|---|---|---|---|---|---|---|---|
| Run Number | 33 | 34 | 35 | 36 | 37 | 38 | 39 | 40 |
| Catalyst | $TiO_2$—5% $MoO_3$ | $TiO_2$—5% $MoO_3$ | $TiO_2$—5% $MoO_3$ | $TiO_2$—10% $MoO_3$ | $TiO_2$—10% $MoO_3$ | $TiO_2$—10% $MoO_3$ | $TiO_2$—10% $MoO_3$ | $TiO_2$—5% $WO_3$ |
| Catalyst Number | 19 | 19 | 19 | 25 | 25 | 25 | 25 | 26 |
| Temperature, °C. | 325 | 350 | 375 | 300 | 325 | 350 | 375 | 325 |
| Aniline Conversion, % | 82 | 64 | 65 | 65 | 60 | 59 | 34 | 91 |
| Ether Conversion, % | 54 | 63 | 92 | 55 | 49 | 57 | 55 | 64 |
| | Product Distribution, wt. percent | | | | | | | |
| N—et aniline | 52.0 | 51.9 | 23.5 | 62.6 | 63.7 | 54.5 | 46.6 | 45.3 |
| o-et aniline | 6.4 | 10.5 | 20.2 | 5.8 | 7.7 | 12.1 | 12.8 | 3.7 |
| p-et aniline | 2.0 | 3.3 | 7.4 | 2.6 | 3.1 | 4.7 | 5.2 | 2.2 |

TABLE II-continued
Alkylations Using Two Metal Oxides One or Both Being a B-Subgroup Metal Oxide Catalyst

| | | | | | | | | |
|---|---|---|---|---|---|---|---|---|
| N,N—di-et aniline | 11.0 | 6.3 | 2.1 | 9.4 | 6.9 | 3.7 | 1.4 | 18.2 |
| 2,6-di-et aniline | 3.5 | 4.3 | 11.5 | 3.1 | 2.9 | 3.6 | 3.7 | 1.9 |
| Other ring di-et anilines | 14.0 | 10.9 | 10.6 | 10.1 | 9.0 | 10.7 | 9.0 | 17.9 |
| Ring tri-et anilines | 3.7 | 2.6 | 4.0 | 1.8 | 1.2 | 1.7 | 2.4 | 6.7 |
| Others | 7.4 | 10.2 | 20.8 | 4.5 | 5.5 | 9.0 | 19.0 | 4.2 |
| N—alkylation, % | 63.0 | 58.2 | 25.6 | 72.0 | 70.6 | 58.2 | 48.0 | 63.5 |
| Ring alkylation, % | 11.9 | 18.1 | 39.1 | 11.5 | 13.7 | 20.4 | 21.7 | 7.8 |
| Di-, tri-, & others, % | 25.1 | 23.7 | 35.4 | 16.4 | 15.7 | 21.4 | 30.4 | 28.8 |
| Ratio of o-et to p-et | 3.2 | 3.2 | 2.7 | 2.2 | 2.5 | 2.6 | 2.5 | 1.7 |
| Gaseous products, mL/hr | 160 | 195 | 550 | 0 | 0 | 200 | 370 | 220 |

| Run Number | 41 | 42 | 43 | 44** | 45 | 46 | 47 | 48 |
|---|---|---|---|---|---|---|---|---|
| Catalyst | $TiO_2$—5% $WO_3$ | $TiO_2$—5% $Fe_2O_3$ | $TiO_2$—5% $Fe_2O_3$ | $TiO_2$—5% $Fe_2O_3$ | $TiO_2$—10% $Fe_2O_3$ | $TiO_2$—10% $Fe_2O_3$ | $TiO_2$—10% $Fe_2O_3$ | $TiO_2$—20% $Fe_2O_3$ |
| Catalyst Number | 26 | 27 | 27 | 27 | 32 | 32 | 32 | 35 |
| Temperature, °C. | 350 | 350 | 375 | 375 | 300 | 350 | 375 | 350 |
| Aniline Conversion, % | 89 | 87 | 78 | 55 | 13 | 31 | 33 | 14 |
| Ether Conversion, % | 89 | 76 | 83 | 78 | 13 | 50 | 69 | 22 |
| Product Distribution, wt. percent | | | | | | | | |
| N—et aniline | 27.8 | 40.5 | 39.8 | 43.0 | 87.7 | 56.2 | 31.3 | 39.2 |
| o-et aniline | 7.7 | 7.7 | 12.0 | 17.9 | 6.4 | 23.4 | 36.4 | 46.6 |
| p-et aniline | 4.3 | 2.3 | 3.1 | 3.8 | — | 5.5 | 6.2 | — |
| N,N—di-et aniline | 7.0 | 10.6 | 6.2 | 3.3 | 0.6 | 1.6 | 1.4 | — |
| 2,6-di-et aniline | 9.0 | 5.4 | 6.5 | 6.1 | — | 3.6 | 4.8 | 2.4 |
| Other ring di-et anilines | 20.3 | 19.7 | 14.1 | 10.5 | — | 6.1 | 5.2 | 3.3 |
| Ring tri-et anilines | 12.5 | 5.4 | 3.5 | 1.7 | — | — | 3.7 | 2.4 |
| Others | 11.3 | 8.4 | 14.9 | 13.8 | 5.3 | 3.7 | 10.9 | 6.0 |
| N—alkylation, % | 34.8 | 51.1 | 46.0 | 46.3 | 88.3 | 57.8 | 32.7 | 39.2 |
| Ring alkylation, % | 21.0 | 15.4 | 21.6 | 27.8 | 6.4 | 32.5 | 47.4 | 49.0 |
| Di-, tri-, & others, % | 44.1 | 33.5 | 32.5 | 26.0 | 5.3 | 9.8 | 19.8 | 11.7 |
| Ratio of o-et to p-et | 1.8 | 3.4 | 3.9 | 4.7 | — | 4.3 | 5.9 | — |
| Gaseous products, mL/hr | 475 | 295 | 415 | 460 | 15 | 450 | 690 | 190 |

| Run Number | 49 | 50 | 51 | 52 | 53 | 54 | 55 | 56 | 57 |
|---|---|---|---|---|---|---|---|---|---|
| Catalyst | $TiO_2$—20% $Fe_2O_3$ | $TiO_2$—10% $Fe_2O_3$ | $TiO_2$—10% $Fe_2O_3$ | $TiO_2$—10% $Fe_2O_3$ | $TiO_2$—10% $Fe_2O_3$ | $ZrO_2$—$TiO_2$ | $ZrO_2$—$TiO_2$ | $ZrO_2$—$TiO_2$ | $ZrO_2$—$TiO_2$ |
| Catalyst Number | 35 | 38 | 38 | 38 | 38 | 50 | 50 | 50 | 50 |
| Temperature, °C. | 375 | 300 | 350 | 375 | 400 | 300 | 350 | 375 | 400 |
| Aniline Conversion, % | 18 | 30 | 66 | 57 | 41 | 1 | 15 | 14 | 11 |
| Ether Conversion, % | 50 | 10 | 65 | 78 | 90 | 5 | 18 | 13 | 15 |
| Product Distribution, wt. percent | | | | | | | | | |
| N—et aniline | 20.6 | 87.3 | 57.1 | 46.8 | 33.4 | 100 | 95.9 | 88.7 | 81.2 |
| o-et aniline | 56.8 | 1.5 | 9.1 | 16.1 | 25.6 | — | — | — | 0.7 |
| p-et aniline | 1.0 | 0.2 | 1.6 | 3.2 | 6.0 | — | — | — | — |
| N,N—di-et aniline | — | 5.5 | 7.8 | 3.0 | 1.0 | — | 2.8 | 1.8 | 1.0 |
| 2,6-di-et aniline | 3.9 | 1.3 | 4.7 | 5.5 | 4.2 | — | — | — | — |
| Other ring di-et anilines | 4.9 | 2.3 | 11.5 | 9.6 | 8.9 | — | — | — | — |
| Ring tri-et anilines | 3.2 | 0.1 | 2.3 | 2.9 | 4.4 | — | — | — | — |
| Others | 9.5 | 1.8 | 5.8 | 12.9 | 16.5 | — | 1.3 | 9.4 | 17.1 |
| N—alkylation, % | 20.6 | 92.8 | 64.9 | 49.8 | 34.4 | 100 | 98.7 | 90.5 | 82.2 |
| Ring alkylation, % | 61.7 | 3.0 | 15.4 | 24.8 | 35.8 | — | — | — | 0.7 |
| Di-, tri-, & others, % | 17.6 | 4.2 | 19.6 | 25.4 | 29.8 | — | 1.3 | 9.4 | 17.1 |
| Ratio of o-et to p-et | 56.8 | 7.5 | 6.1 | 5.0 | 4.3 | — | — | — | — |
| Gaseous products, mL/hr | 410 | 40 | 350 | 620 | 990 | 30 | 110 | 110 | 160 |

**Water was included in the reactant feed so that the molar ratio of $H_2O$:aniline:ether was 5:1:2.5.

In another series of alkylations various different ether alkylating agents were used in reactions with aniline. In these experiments the following ethers were employed: tetrahydrofuran (THF), dibutyl ether (bu₂O), tetrahydropyran (THP), and 1,4-dioxane (dioxane). The results of these experiments are set forth in Table III.

TABLE III
Alkylations Using Other Ether Alkylating Agents

| Run Number | 58 | 59 | 60 | 61 | 62 | 63 |
|---|---|---|---|---|---|---|
| Alkylating Agent | THF | Bu₂O | Bu₂O | THF | THP | Dioxane |
| Catalyst Number | 19 | 19 | 19 | 22 | 22 | 22 |
| Temperature, °C. | 350 | 350 | 400 | 250 | 300 | 300 |
| Ether:aniline mole ratio | 3:1 | 1:1 | 1:1 | 3:1 | 3:1 | 2:1 |
| Aniline Conversion, % | 91 | 36 | 30 | 98 | 74 | 32 |
| Ether Conversion, % | 83 | 66 | 96 | 43 | 46 | 24 |
| Product Distribution, wt. percent | | | | | | |
| N—et aniline | | | | | | 19.0 |
| o-et aniline | | | | | | 5.6 |
| p-et aniline | | | | | | 16.1 |
| N,N—di-et aniline | | | | | | — |
| 2,6-di-et aniline | | | | | | 3.9 |
| Other di-et anilines | | | | | | 11.9 |
| Ring bu anilines | | | 25.7 | | | |
| N—bu aniline | 1.7 | 24.8 | 20.6 | | | |
| 1-phenyl pyrrole | 5.0 | | | | | |
| 1-phenyl pyrrolidine | 65.0 | | | 96.8 | | 17.8 |
| 1-phenyl piperidine | | | | | 97.9 | |
| Others | 28.3 | 75.2 | 53.7 | 3.2 | 2.1 | 25.6 |
| N—alkylation, % | | | | | | 19.0 |
| Ring alkylation, % | | | | | | 25.6 |
| Di-, tri- & others, % | | | | | | 55.3 |
| Ratio of o-et | | | | | | 0.3 |

TABLE III-continued

| Alkylations Using Other Ether Alkylating Agents | | | | | | |
|---|---|---|---|---|---|---|
| Run Number | 58 | 59 | 60 | 61 | 62 | 63 |
| to p-et | | | | | | |
| Gaseous products, mL/hr | | | | | | 100 |

Table IV summarizes the results of additional runs in which N-ethylaniline was alkylated with diethyl ether (Runs 64–68) and 2,6-diethylaniline was alkylated with dimethyl ether (Runs 69–70) using several different catalysts based on titanium dioxide. In Runs 64–68, the reactants were fed in a ratio of 2 moles of the ether per mole of the nailine reactant. In Runs 69 and 70 this ratio was 2.5 to 1.

TABLE IV

| Alkylations of Substituted Anilines | | | | | | | |
|---|---|---|---|---|---|---|---|
| Run Number | 64 | 65 | 66 | 67 | 68 | 69 | 70 |
| Catalyst Number | 24 | 24 | 19 | 19 | 32 | 21 | 21 |
| Temperature, °C. | 350 | 400 | 350 | 400 | 375 | 250 | 300 |
| Amine Conversion, % | 30 | 51 | 63 | 88 | 39 | 43 | 86 |
| Ether Conversion, % | 54 | 93 | 71 | 98 | 40 | | |
| Product Distribution, wt. percent | | | | | | | |
| Aniline | 5.1 | 19.8 | 25.6 | 48.4 | 33.0 | | |
| N—et aniline | 69.5 | 48.6 | 37.5 | 12.5 | 60.6 | | |
| o-et aniline | 1.7 | 5.9 | 4.4 | 11.7 | 1.6 | | |
| p-et aniline | 0.9 | 3.1 | 1.7 | 6.4 | 0.2 | | |
| N,N—di-et aniline | 12.4 | 4.9 | 6.1 | 0.9 | 1.2 | | |
| 2,6-di-et aniline | 0.8 | 2.2 | 1.7 | 3.1 | 0.4 | | |
| Other di-et anilines | 6.3 | 8.3 | 6.7 | 4.1 | 1.0 | | |
| 4-me-2,6-di-et aniline | | | | | | | 2 |
| N—me-2,6-di-et aniline | | | | | | 42 | 13 |
| N,N—di-me-2,6-di-et aniline | | | | | | 58 | 26 |
| N,4-di-me-2,6-di-et aniline | | | | | | | 15 |
| N,N,4-tri-me-2,6-di-et aniline | | | | | | | 44 |
| Others | 3.3 | 7.2 | 16.3 | 12.9 | 1.9 | | |
| N—alkylation, % | 12.4 | 4.9 | 6.1 | 0.9 | 1.2 | 100 | 39 |
| Ring alkylation, % | 3.4 | 11.2 | 7.8 | 21.2 | 2.2 | | 61 |
| Di-, tri- & others, % | 9.2 | 15.5 | 23.0 | 17.0 | 3.0 | | |
| Ratio of o-et to p-et | 1.9 | 1.9 | 2.6 | 1.8 | 8.0 | — | 120 |
| Gaseous products, mL/hr | 200 | 140 | 360 | 710 | 330 | | |

In contrast to the results reported above, extensive amounts of decomposition of the alkylating agent were encountered when using an alcohol as the alkylating agent and an iron oxide-germanium oxide catalyst in accordance with the prior art. See in this connection U.S. Pat. No. 4,351,958. In particular, when ethanol and aniline were reacted in the above manner at 350 C. over a catalyst composed of 96.1 weight percent $Fe_2O_3$ and 3.9 weight percent $GeO_2$, non-condensable gases were evolved at the rate of 1800 mL/hr. In fact, no ethanol passed through the reaction zone—the ethanol which did not react with the aniline was completely destroyed.

As noted above, the inclusion of water in the feed to the catalyst can be helpful insofar as the regiochemical aspects of the process are concerned. For example a comparison of Runs 43 and 44 in Table II shows that the presence of water resulted in an increase in the ratio of o-ethylaniline to p-ethylaniline from 3.9 to 4.7. When water is employed, it will normally be used in amounts no higher than about 10 moles per mole of ether used, preferably in amounts falling in the range of about 0.1 to about 5 moles per mole of ether used.

The conditions used in the process of this invention are susceptible to considerable variation. For example, while my process is usually conducted with an excess of the ether reactant relative to the aromatic amine reactant, a stoichiometric deficiency of the ether may be used, especially when seeking to maximize monoalkylation and minimize polyalkylation. Likewise, the ratio used will be influenced to some extent by the composition of the amine (i.e., whether it is a monoamine or a polyamine), the composition of the ether (i.e., whether it is a monoether or a polyether), and the extent and type of alkylation (i.e., nuclear alkylation and/or N-alkylation) desired. In most cases, the reaction mixture will contain about 0.5 to about 5 molar equivalents of the ether per molar equivalent of the amine. In the case of reactions between monoethers and monoamines, the molar ratio of ether to amine is preferably in the range of about 1:1 to about 3:1.

It is possible to vary certain aspects and other features of the above described invention without departing from the lawful scope or true spirit thereof.

I claim:

1. A process for alkylating aromatic amines comprising the step of reacting at a temperature within the range of from about 300°–400° C. (a) an aromatic amine having at least one primary amino group on an aromatic ring and having a replaceable hydrogen atom on the ring in at least an ortho or para position relative to such amino group, with (b) an acyclic ether, in the presence of a mixed metal oxide alkylation catalyst consisting essentially of between about 70 to 100 mole % of a Group IV-B metal oxide and between 0 to about 30 mole % of (i) a Group VI-B metal oxide, or (ii) a Group VIII metal oxide, or (iii) a mixture of (i) and (ii) so that alkylation of the aromatic amine occurs.

2. A process of claim 1 wherein the catalyst consists essentially of a mixture of a titanium oxide and a molybdenum oxide.

3. A process of claim 2 wherein the catalyst consists essentially of a mixture of $TiO_2$ and $MoO_3$.

4. A process of claim 1 wherein the catalyst consists of essentially of a mixture of titanium oxide and an iron oxide.

5. A process of claim 4 wherein the catalyst consists essentially of a mixture of $TiO_2$ and $Fe_2O_3$.

6. A process of claim 1 wherein the reaction is conducted in the vapor phase in the presence of water vapor.

7. A process of claim 1 wherein the ether is a dialkyl ether in which at least one of the alkyl groups is methyl, ethyl or propyl.

8. A process of claim 1 wherein the amine is a mononuclear primary aromatic amine having one or two amino groups on the aromatic ring.

9. A process of claim 8 wherein the amine is aniline, one or a mixture of two or more toluidine isomers or one or a mixture of two or more xylidine isomers, and the ether is dimethyl ether, diethyl ether or dipropyl ether.

10. A process of claim 1 wherein the reaction is conducted in the vapor phase by contacting a vapor phase mixture of the amine and the ether with a bed of the catalyst.

11. A process of claim 1 wherein the catalyst comprises at least about 80% by weight of titanium dioxide and up to about 20% by weight of molybdenum trioxide, tungsten, trioxide, ferric oxide or a mixture of any two or all three of them.

12. A process of claim 1 wherein the amine is aniline, one or a mixture of two or more toluidine isomers or one or a mixture of two or more xylidine isomers, and the ether is a dimethyl ether or diethyl ether.

13. A process of claim 1 wherein the catalyst consists essentially of titanium dioxide and molybdenum trioxide, and the amine is (a) aniline, (b) one or a mixture of two or more toluidine isomers or (c) one or a mixture of two or more xylidine isomers.

* * * * *